(12) United States Patent
Leeds et al.

(10) Patent No.: US 8,803,094 B2
(45) Date of Patent: Aug. 12, 2014

(54) CARBON NANOTUBE COMPOSITIONS AND METHODS OF MAKING AND USING SAME

(71) Applicants: Jarrett Leeds, College Park, MD (US); YuHuang Wang, Laurel, MD (US); John T. Fourkas, Bethesda, MD (US)

(72) Inventors: Jarrett Leeds, College Park, MD (US); YuHuang Wang, Laurel, MD (US); John T. Fourkas, Bethesda, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 13/899,052

(22) Filed: May 21, 2013

(65) Prior Publication Data

US 2013/0306870 A1 Nov. 21, 2013

Related U.S. Application Data

(60) Provisional application No. 61/649,732, filed on May 21, 2012.

(51) Int. Cl.
*G01J 5/02* (2006.01)
(52) U.S. Cl.
USPC .................................................. 250/339.01
(58) Field of Classification Search
USPC ...................................... 250/339.01–339.15
See application file for complete search history.

(56) References Cited

U.S. PATENT DOCUMENTS

| | | | | |
|---|---|---|---|---|
| 7,601,421 B2 * | 10/2009 | Khabashesku et al. | .... | 428/297.4 |
| 7,733,479 B2 * | 6/2010 | Shew et al. | .................. | 356/244 |
| 7,939,047 B2 * | 5/2011 | Tour et al. | ..................... | 423/460 |
| 8,187,703 B2 * | 5/2012 | Zhu et al. | ................... | 428/297.4 |
| 8,193,430 B2 | 6/2012 | Papadimitrakopoulos et al. | | |
| 8,415,423 B2 * | 4/2013 | Shimizu et al. | ............... | 524/545 |
| 2006/0166003 A1 * | 7/2006 | Khabashesku et al. | ........ | 428/413 |
| 2007/0292896 A1 * | 12/2007 | Strano et al. | ................... | 435/7.9 |
| 2008/0260616 A1 * | 10/2008 | Tour et al. | .................. | 423/447.1 |
| 2010/0080978 A1 * | 4/2010 | Jerome et al. | ............. | 428/317.9 |
| 2010/0143701 A1 * | 6/2010 | Zhu et al. | ...................... | 428/323 |
| 2012/0071610 A1 * | 3/2012 | Nicholas | .................... | 525/331.9 |
| 2012/0138589 A1 * | 6/2012 | Mitchell et al. | ............... | 219/202 |

OTHER PUBLICATIONS

Angelikopoulos, et al. "Dispersing Individual Single-Wall Carbon Nanotubes in Aqueous Surfactant Solutions below the cmc" J. Phys. Chem. (2010) 114, 2-9.
Moore, et al. "Individually Suspended Single-Walled Carbon Nanotubes in Various Surfactants", (2003) Nano Lett. vol. 3, No. 10, pp. 1379-1382.

* cited by examiner

*Primary Examiner* — Kiho Kim
(74) *Attorney, Agent, or Firm* — Hodgson Russ LLP

(57) ABSTRACT

Carbon nanotube compositions suitable for printing, methods of making carbon nanotube compositions, and substrates having a print thereon containing carbon nanotube compositions, and uses thereof. The carbon nanotubes of the compositions are individualized. The carbon nanotube compositions can be used in applications, such as document security.

17 Claims, 9 Drawing Sheets

US 8,803,094 B2

CARBON NANOTUBE COMPOSITIONS AND METHODS OF MAKING AND USING SAME

CROSS-REFERENCE TO RELATED APPLICATIONS

This application claims priority to U.S. Provisional Application No. 61/649,732, filed on May 21, 2012, the disclosure of which is incorporated herein by reference.

STATEMENT REGARDING FEDERALLY SPONSORED RESEARCH

This disclosure was made with government support under contract no. NSF CHE1055514 awarded by the National Science Foundation and contract no. N000141110465 awarded by the Office of Naval Research. The government has certain rights in the disclosure.

FIELD OF THE DISCLOSURE

The instant disclosure generally relates to printing compositions. More particularly the disclosure relates to printing compositions and materials comprising carbon nanotubes and uses of such compositions.

BACKGROUND OF THE DISCLOSURE

Single-walled carbon nanotubes (SWCNTs) have remarkable electrical and optical properties, particularly when they are individually dispersed. However, high concentrations of individually dispersed nanotubes have been difficult to attain, which has hampered the adoption of solution-based technologies such as self-assembly, thin-film coating, fiber spinning, and printing. In addition to individually dispersed solutions, recent work in thin-film transistor devices has underscored the need for producing bulk quantities of nanotubes that can remain individually dispersed after drying and/or curing.

One of the interesting properties of SWCNTs is the optical absorption and emission features that are associated with the electronic transitions between van Hove singularities (kinks) in the density of states. These optical properties make it possible to take advantage of the unique near-infrared (NIR) fluorescence of SWCNTs as a spectral signature in applications such as document security. Tuning of the band-gap fluorescence by the surrounding environment or through chemical doping methods also enables nanotube applications such as bio-optical sensors. However, these sharp optical absorption features appear only when the nanotubes are well dispersed. Due to coupling of electronic states, fluorescence is often completely quenched when nanotubes are bundled, especially when metallic nanotubes are present. Thus, there is a need for improved nanotube compositions and methods of using them, which is addressed by the present disclosure.

BRIEF SUMMARY OF THE DISCLOSURE

In an aspect the disclosure provides a composition suitable for printing comprising a plurality of carbon nanotubes in an aqueous medium, said medium comprising a polyol and a surfactant. The concentration of the nanotubes in the composition is at least 3.6 µg/L and at least 20% of the nanotubes are individually dispersed.

In an aspect the disclosure provides a substrate having a print on at least a portion thereof, where the print is made from a composition of the present disclosure.

In an aspect, the present disclosure provides a method for detecting the presence of a plurality of single-walled carbon nanotubes deposited on a substrate from a composition comprising a plurality of the single-walled carbon nanotubes in a aqueous medium, said medium comprising a polyol and a surfactant. The concentration of the nanotubes in the composition is at least 3.6 µg/L mg/L and at least 20% of the nanotubes are individually dispersed comprising the steps of: a) obtaining a near-infrared spectrum of a sample ink; b) determining if the sample ink has one or more preselected peaks in the near-infrared spectrum; and c) identifying the ink as the single-walled carbon nanotube composition if the sample has one or more preselected peaks in the near-infrared spectrum.

shows fluorescence of nanotube species before washing; (B) indicates that tubes are individually dispersed to a high degree. After washing away the sucrose matrix with an ethanol-water mixture (C) the nanotubes bundle eliminating the sharp fluorescence peaks (D).

Figure 8:
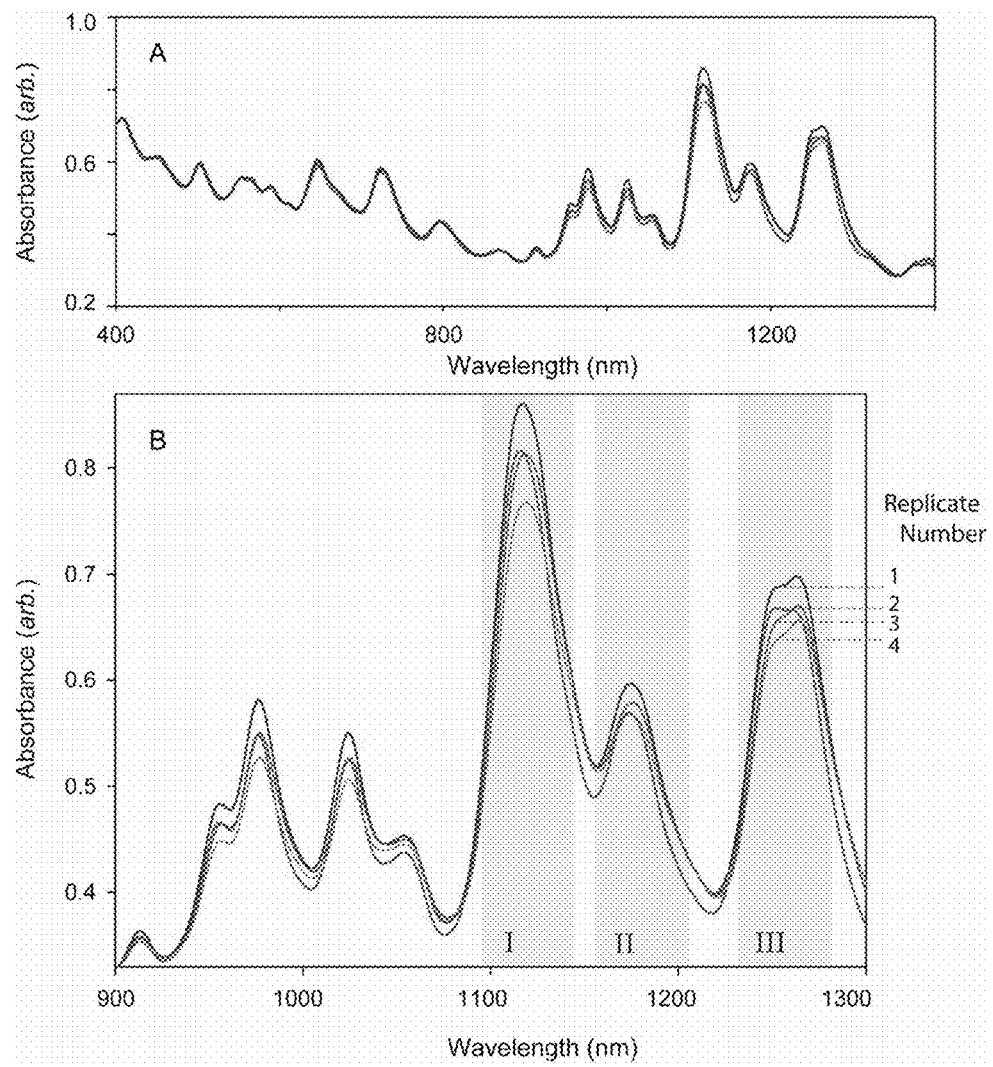

FIG. 8 shows a representative absorption spectra of 4 replicate SWCNT/SDBS-sucrose samples prepared on different days with the same batch of HiPco nanotubes. Slight variations in the final concentration have been accounted for by varying the dilution factor from 3.2×-5.0× to normalize the solutions to an absorbance of 0.592 at 500 nm. Only a small variance in the absorption of the four replicates can be seen in the visible region of the spectra (A) which consists mainly of $E_{22}$ transition. However, there exists a large statistical variance in the NIR region (B), where the peaks correspond mainly to $E_{11}$ transitions. Evaluating the fluorescence excitation-emission maps for these solutions, the number of species in each of shaded regions I, II, and III can be shown to be 3, 2 and 4, respectively, causing the peaks to be highly asymmetric. In region III, replicates 1, 3 and 4 appear to be red shifted from replicate 2, an illusion that is created due to the distribution of nanotubes being skewed toward species with lower-energy $E_{22}$ transitions. This same phenomenon is evident in regions I and II to a lesser degree.

Figure 9:
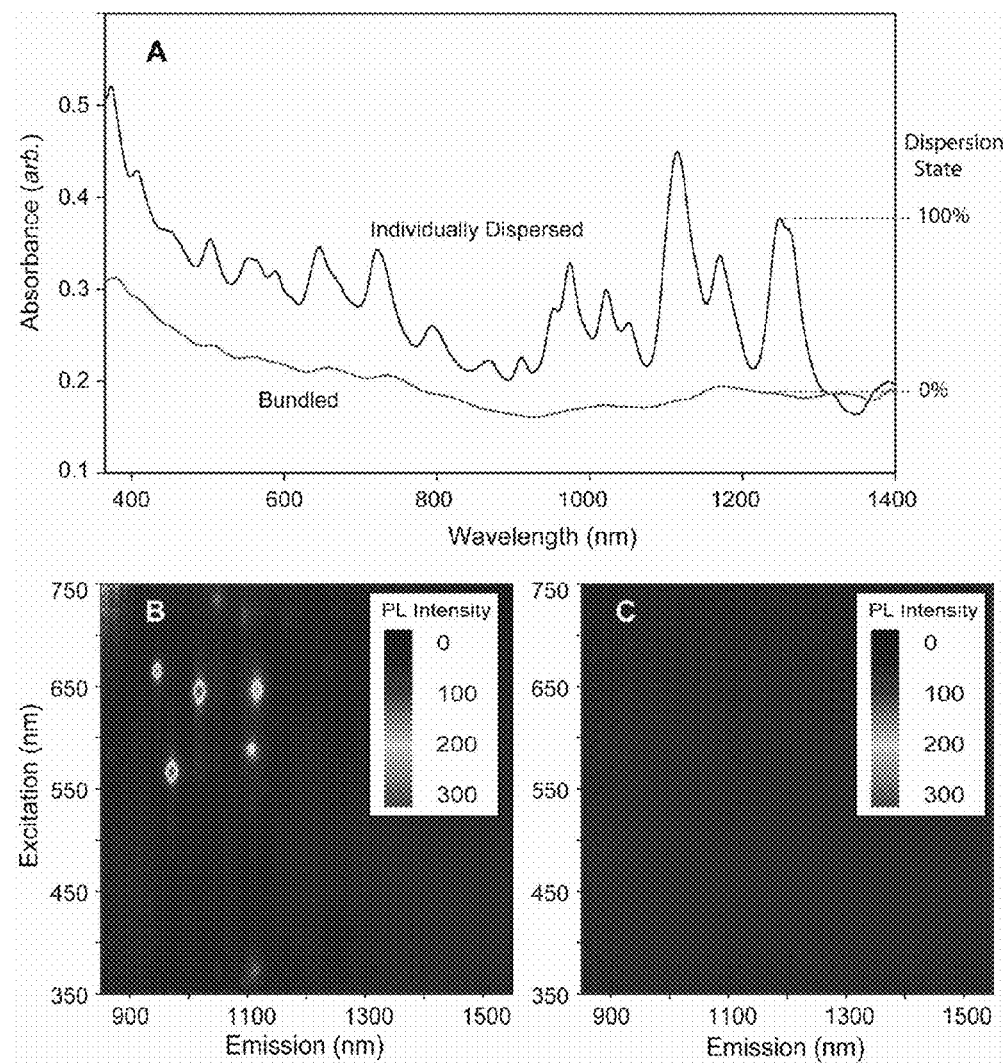

FIG. 9 shows representative absorption spectrum (A) of individually dispersed carbon nanotubes contrasted to that of bundled nanotubes. The sharp peaks arising from excitonic transitions between van Hove singularities are mostly absent in the bundled spectra. The photoluminescence (PL) excitation-emission map of individually dispersed (B) nanotubes has sharp emission peaks arising from individual semiconducting nanotubes. When nanotubes bundle, fluorescence is almost non-existent (C).

Figure 10:
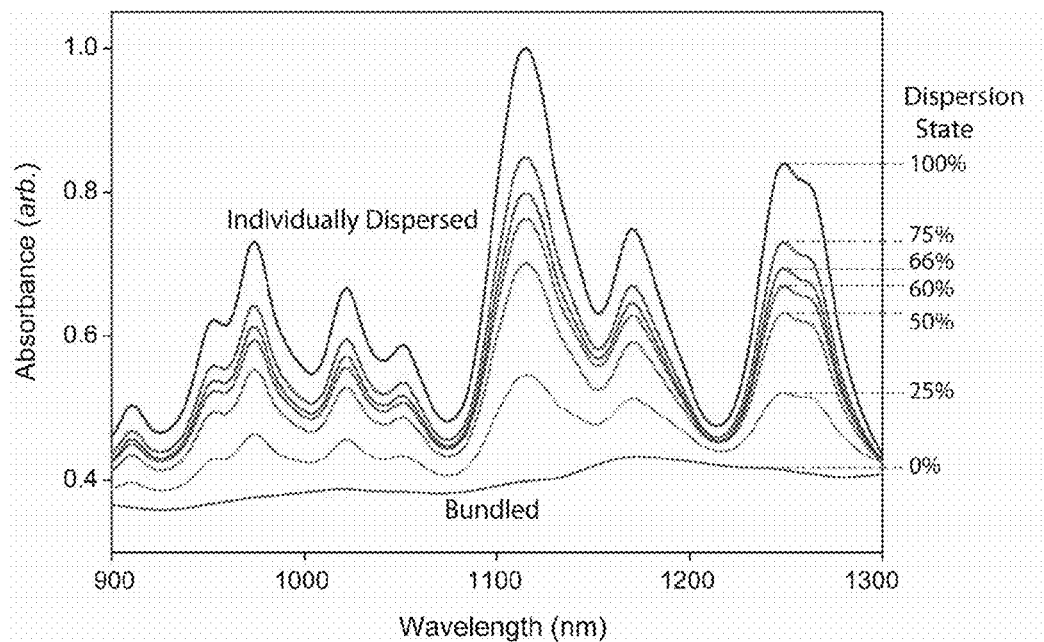

FIG. 10 shows representative absorption spectra of different dispersion states of carbon nanotubes made by diluting a solution of individually dispersed nanotubes with a solution containing only bundled nanotubes. As the dispersion state percentage, or number of individual nanotubes in solution decreases, peak intensities drop and broaden.

Figure 11:
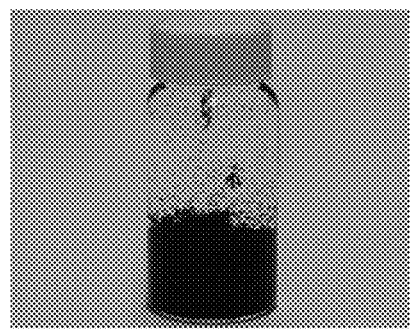

FIG. 11 shows a representative SWCNT solution post-sonication. Without a surfactant, sucrose solution failed to disperse SWCNTs during sonication.

Figure 12:
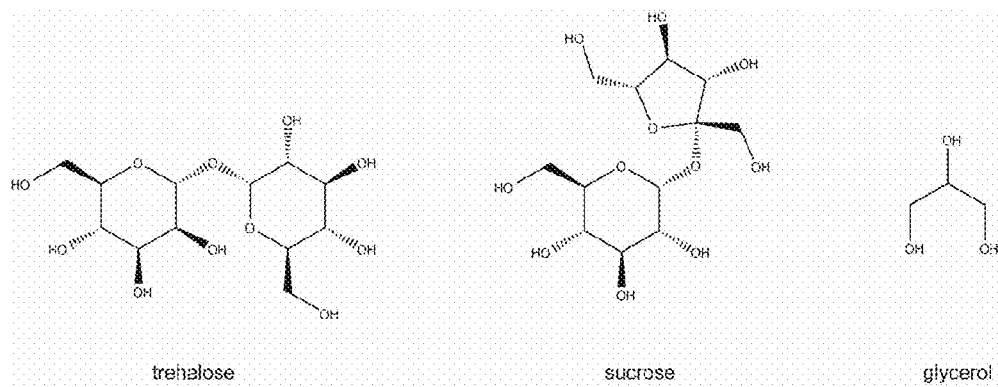

FIG. 12 shows representative molecular structures of polyols used in the experiments.

Figure 13:
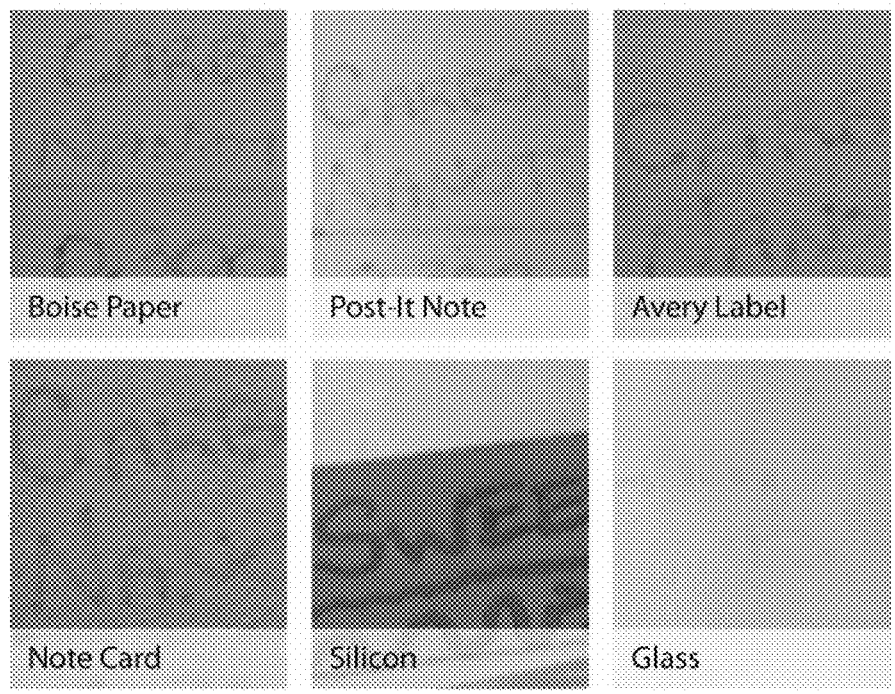

FIG. 13 shows representative SWCNT/SDBS-sucrose solutions that were used as an ink in a 300 μm technical pen. Several substrates were written on using the SWCNT/SDBS-sucrose ink including paper products, silicon and glass.

Figure 14:
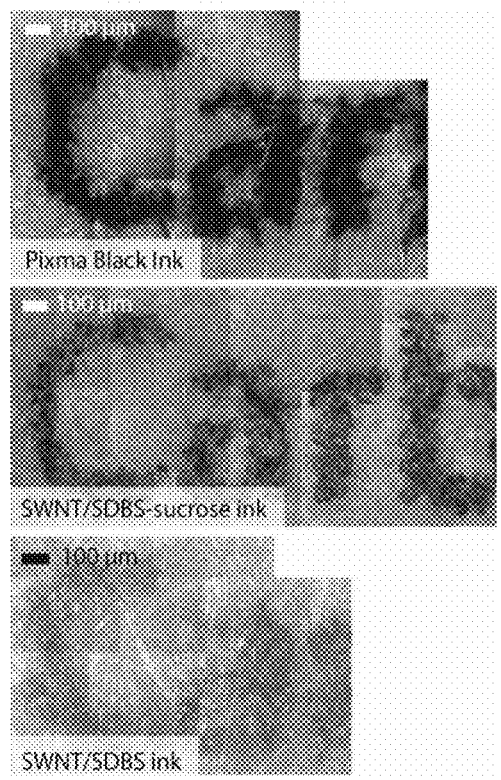

FIG. 14 shows a representative composite optical micrographs of the word 'Carbon' inkjet-printed on paper using Canon PIXMA black ink (stock), SWCNT/SDBS-sucrose ink and SWCNT/SDBS ink (control). The SWCNT-based ink jetted with a uniform coating on the substrate, comparable to the PIXMA black ink.

Figure 15:
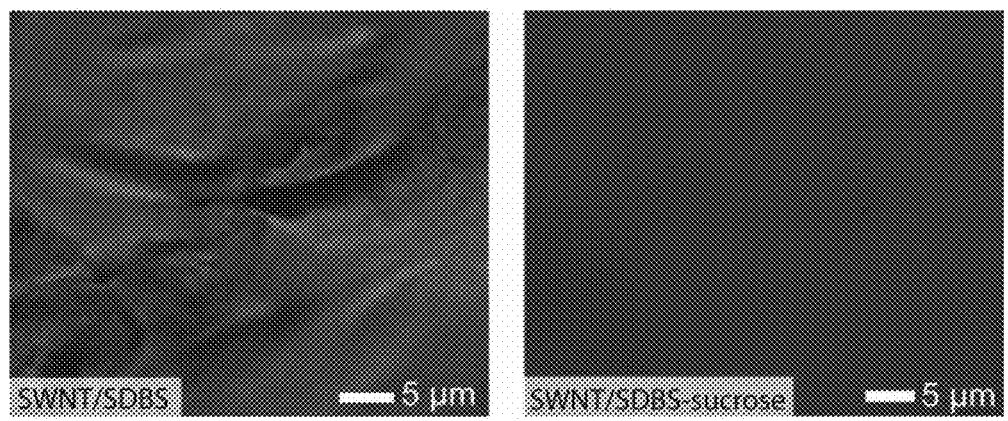

FIG. 15 shows a representative drop cast solutions of SWCNT/SDBS (left) and SWCNT/SDBS-sucrose (right). Sucrose keeps the SWCNTs from bundling creating a uniform film upon drying.

Figure 16:
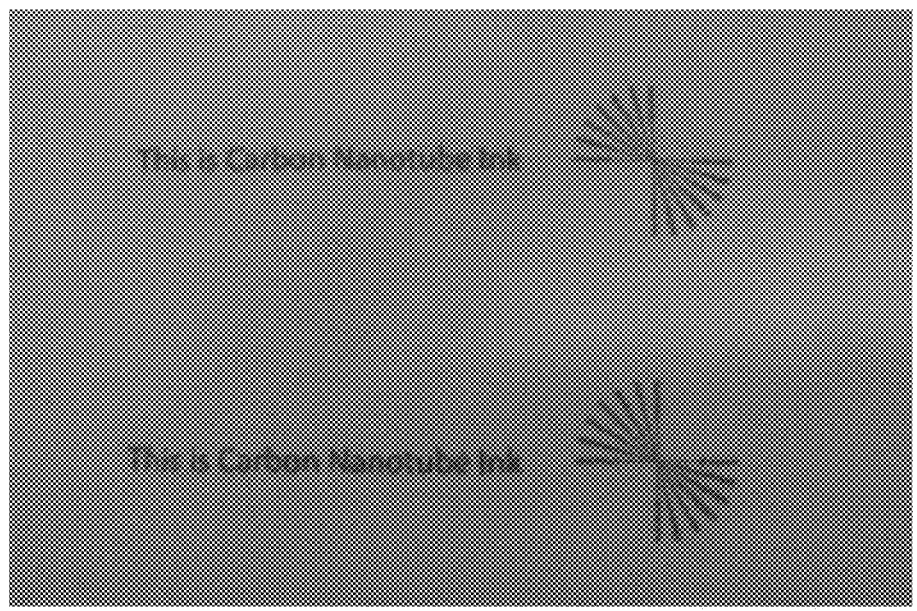

FIG. 16 shows a representative inkjet-printed characters and pattern using SWCNT/SDBS-sucrose based ink.

Figure 17:
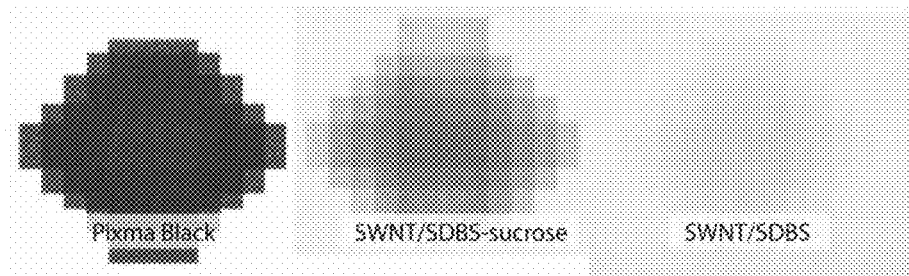

FIG. 17 shows a representative inkjet-printed geometric patterns of PIXMA ink, SWCNT/SDBS-sucrose ink and SWCNT/SDBS ink.

DETAILED DESCRIPTION OF THE DISCLOSURE

In an embodiment, the present disclosure provides compositions comprising individually dispersed carbon nanotubes and methods for making and using the same. The compositions may be used for printing applications which may include aspects of document security.

In an aspect, the disclosure provides a composition suitable for printing. The composition comprises a plurality of individually dispersed carbon nanotubes in an aqueous medium comprising a polyol and a surfactant.

The carbon nanotubes may be single-walled nanotubes (SWCNTs) and multi-walled carbon nanotubes (MWCNTs). The term "single walled" as used herein in conjunction with carbon nanotubes refers to carbon nanotubes having a single carbon wall. The nanotubes can vary in diameter and length. In embodiments, the diameter of the nanotubes can be 0.4 to 3 nm including all values to the 0.01 nm and ranges therebetween. In embodiments, the length of the carbon nanotubes can be from 20 to 10,000 nm and all values to the nm and ranges therebetween. It is realized that extraneous impurities, such as catalyst metal particles, fullerenic carbon, amorphous carbon, graphitic carbon, and carbon onions, can be present to different degrees in prepared raw carbon nanotube samples. SWCNT materials are often a mixture of both semiconducting and metallic types. In an embodiment, it is desirable that 80 to 99.9% of the metal form of carbon nanotubes are removed from the plurality of carbon nanotubes. In an embodiment, purified SWCNTs can be used. Methods for purification of commercially available or laboratory prepared nanotubes are known in the art.

An aqueous medium is used for preparing the composition of the present disclosure. In an embodiment, the aqueous medium comprises at least 80%, 85%, 90%, 95%, or 99% water ($H_2O$) and all integer percent values and ranges therebetween. In another embodiment, the aqueous medium comprises 100% water. In an embodiment, the water can be heavy water, dueterium oxide ($D_2O$). In various embodiments, nanopure, distilled, or deionized water can be used. In an embodiment, carrier solvents of the various reagents can be present in the aqueous medium. For example, the carrier solvent can be an alcohol such as ethanol.

The aqueous medium comprises one or more polyols. In one embodiment, the polyol has two or more alcohol substituents. In another embodiment, the polyol has three or more alcohol substituents. The polyol can be, for example, a $C_2$ to $C_{10}$ linear or branched aliphatic polyol, a $C_5$ to $C_{30}$ cyclic or polycyclic aliphatic polyol, or a combination thereof. In another embodiment, the polyol can be a monosaccharide, disaccharide, trisaccharide, or a combination thereof. Examples of suitable polyols include sucrose, trehalose, glycerol, or combinations thereof. The concentration of the polyol may vary. In an embodiment, the concentration is below the aqueous solubility of the polyol. In an embodiment, the concentration of the polyol in the aqueous medium is from 10 to 25% by weight in the aqueous medium. While not intending to be bound by any particular theory, it is considered that the polyol does not undergo any charge transfer or have any electronic interaction with the nanotubes.

In an embodiment, the disclosure provides a composition comprising an aqueous medium consisting essentially of water, a polyol and surfactant. In an embodiment, a composition does not contain any ingredient that will disrupt or interfere with the arrangement of surfactant surrounding the carbon nanotubes or result in arrangements where the nanotubes are not individually dispersed or are surrounded by inhomogenously distributed non-surfactant molecules. For example, flavin moieties are known to form composites of nanotube bundles by surrounding the bundles. Therefore in an embodiment the composition does not contain flavin moieties. In embodiments, the disclosure includes methods for making compositions of the disclosure without the use of flavin moities. In yet another embodiment, the disclosure provides a composition consisting essentially of a plurality of carbon nanotubes in a aqueous medium, said medium consisting essentially of a polyol and a surfactant.

The target viscosity can vary. In an example, a 24.7% w/w sucrose solution, which without SDBS, had a viscosity of about 2.4 $\eta/\eta_w$ (i.e., the viscosity is 2.4 times that of water) was used. In an embodiment, the range of viscosities of the polyol solution (i.e., polyol in aqueous medium before the surfactant and nanotubes are added) that can be used can be from 1.3 to 2.4 $\eta/\eta_w$ and all values to the 0.1 and ranges therebetween.

The aqueous medium also comprises a surfactant. Examples of suitable classes of surfactants include anionic, cationic, and nonionic surfactants. In an embodiment, the surfactant can be an alkyl sulfonate or alkaryl sulfonate surfactant. For example, the surfactant can be SDBS, sodium dodecylsulfate (SDS), sodium dodecylsulfonate (SDSA), sodium n-lauroylsacrosinate (e.g., Sarkosyl®), sodium alkyl allyl sulfosuccinate (e.g., TREM®), poly (styrene sulfonate) sodium salt (PSS), dodecyltrimethylammonium bromide (DTAB), cetyltrimethylamminoium bromide (CTAB), Brij® (e.g., Brij® 78, Brij® 700), Triton® X (e.g., Triton® X-100, Triton® X-114, Triton® X-405), PVP (e.g., PVP-10, PVP-40, PVP-1300, polyethylene oxide-polyproylene oxide-polyethylene oxide (PEO-PPO-PEO triblock polymer) (Pluronic®) (e.g., Pluronic® P103, Pluronic® P104 Pluronic® P105 Pluronic® P108, Pluronic® F98, Pluronic® F68, Pluronic® F127, Pluronic® F87, Pluronic® F77, Pluronic® F85), polyethylene oxide-polybutylene oxide-polyethylene oxide (PEO-PBO-PEO triblock polymer) (e.g., EBE), Tween® (e.g., Tween® 20, Tween® 40 Tween® 60, Tween® 80, Tween® 85), and sodium cholate. Combinations of surfactants can also be used. Suitable surfactants are commercially available or can be made by methods known in the art. The concentration of the surfactant may vary. In an embodiment, the concentration of the surfactant is above 0.5 times the critical micelle concentration of the surfactant and below the aqueous solubility of the surfactant. In another embodiment, the concentration of the surfactant is from 1 to 2% by weight in the aqueous medium.

In an aspect, the disclosure provides a method for preparing a composition suitable for printing or other applications. In an embodiment, the method comprises the steps of: a) providing a mixture comprising: a plurality of carbon nanotubes in an aqueous medium which comprises a polyol and a surfactant; and b) effecting the disruption of the nanotubes such that such that a plurality of individually dispersed carbon nanotubes are produced. In various embodiments, the carbon nanotubes may be single walled, multiwalled or combinations thereof. In an embodiment, the disruption is achieved by sonication. Disruption can be carried out at any temperature at which the aqueous medium in a liquid form. For example, if sonication is used, it can be carried out at from 0° C. to 85° C. including all integer values to the ° C. and ranges therebetween. In an embodiment, the sonication can be conducted at from 7 to 15° C. including all integer values to the ° C. and ranges therebetween. Sonication times can vary. Sonication can be conducted from a few minutes to a few hours. For example sonication can be carried out for 1 hour, 2 hours, 3 hours, or until no appreciable increase in the dispersion of nanotubes is noted. Sonication may be carried out as a single step or in multiple steps.

In another embodiment, the method comprises preparing an aqueous medium by adding a polyol and a surfactant to an aqueous liquid (such as water), and then adding carbon nanotubes to the aqueous medium. It will be recognized that the various components of the present composition may be added in any order to achieve the same end result.

By the method of the present disclosure, a composition can be obtained which comprises individually dispersed carbon nanotubes. The individually dispersed nanotubes maybe single walled, multiwalled or combinations thereof. Dispersion is a measure of the extent to which the nanotubes exist in individualized form. While not intending to be bound by any particular theory, it is considered that prior to processing according to a method described herein, the nanotubes exist as a bundled material where the individual nanotubes are held together in rope-like structures. Processing disrupts the rope like structures up by pulling the nanotubes apart (separating them) into smaller and smaller bundles until ideally the nanotubes are individualized. As used herein, the term "substantially dispersed" means that at least 20% of the plurality of carbon nanotubes are individually dispersed (i.e., not in physical contact with each other) in the aqueous medium. In various embodiments, at least 20%, 30%, 40%, 50%, 60%, 70%, 80%, 90%, 95%, 96%, 97%, 98%, or 99% and all integer values to the percent of carbon nanotubes are individually dispersed in the aqueous medium. The dispersion of the nanotubes can be measured by methods known in the art. For example, the dispersion can be measured through optical properties such as fluorescence or photoluminescence, gravimetrically, and by microscopy (e.g., atomic force microscopy (AFM)).

In an embodiment, the method further comprises the step of ultra-centrifuging the sonicated mixture. It is believed that ultra-centrifuging the sonicated mixture aids in removing impurities such as catalyst particles (i.e., Fe impurities), amorphous carbon existing in the initial raw carbon nanotube material, and also aids in removing bundled carbon nanotubes from the solution. Ultracentrifugation conditions may be selected to achieve the optimal results. In an example, the centrifugation involves 122 kg×g of centrifugal force for 4 hours.

In the present disclosure, substantially dispersed carbon nanotubes can be obtained even at high concentrations of the nanotubes. In an embodiment, substantially dispersed carbon nanotubes are present at nanotube concentrations of at least 3.6 µg/L, 10 µg/L, 100 µg/L, 500 µg/L, 1 mg/L, 10 mg/L, 100 mg/L, 1.0 g/L, 1.5 g/L, 3.0 g/L, 5.0 g/L, or 10 g/L and all concentrations to the µg/L. In an embodiment, the plurality of substantially dispersed carbon nanotubes are present at nanotube concentrations from 10 mg/L to 10 g/L and all integer values to the milligram and ranges therebetween. In various embodiments, the plurality of substantially dispersed carbon nanotubes can be present at from 10 mg/L to 5.0 g/L, 10 mg/L to 3.0 g/L, or 100 mg/L to 1.0 g/L and all integer values to the milligram and ranges therebetween for each of the foregoing ranges. In these embodiments, the individually dispersed nanotubes may be single walled and/or multiwalled.

The compositions of the present disclosure can be used as an ink, e.g., for applying markings or printing on substrates. The application may be done by any means suitable for applying markings or printings. For example, the application on a substrate may be done manually or by using automated devices or machines used for such purposes.

In an embodiment, the present disclosure provides a method for printing comprising the steps of preparing a composition suitable for printing comprising individually dispersed carbon nanotubes in an aqueous medium comprising a polyol and a surfactant, optionally removing impurities, and depositing the composition on a substrate in a desired pattern or print.

A wide variety of substrates can be used. The substrates can be flat, stiff, flexible, rough, smooth, or patterned. Examples of suitable substrate materials include cellulosic materials (e.g., paper, cardboard etc.—coated or uncoated, wood), polymer substrates (e.g., plastics, PET, and acrylic), glass, metals, silicon, quartz, or any other suitable substrate known in the art. In an embodiment, the substrate is paper. Combinations of substrates may be used. In various embodiments, the present disclosure provides substrates onto which a composition of the disclosure has been deposited.

The step of depositing the composition comprising the plurality of carbon nanotubes onto a substrate can be by way of any number of standard printing techniques. For example, such techniques include writing, coating, inkjet printing, screen printing (e.g., with a mayer rod), lithographic techniques, brushing, spraying, flowing ink pens, stamping, electrophoretic deposition, and wet spinning In an embodiment, the composition deposited on a substrate is in the form of a film. The film may be of any depth or width. For example, the film may form a pattern on a substrate or the letters of an alphabet. In an embodiment, the film may be a thin film on a substrate. The thin film can be patterned.

In an aspect, the disclosure provides a closed vessel containing the carbon nanotube composition suitable for printing. The vessel can be, for example, a disposable or reusable ink cartridge or a writing instrument.

Individually dispersed single walled carbon nanotubes have unique photoluminescence properties in the near infrared (NIR) spectral region. It was unexpectedly observed that the introduction of viscosity-enhancing compounds (i.e., polyols) such as sucrose can increase the maximum concentration of surfactant-dispersed single-walled carbon nanotubes by more than a factor of 100 while still retaining the optical properties of individual nanotubes. When these solutions are used as inks for methods such as inkjet printing, they retain their fluorescent properties even after the ink has dried.

In an embodiment, the compositions comprises sufficient quantity of individually dispersed single walled nanotubes so that detectable NIR fluorescence is generated from the printed substrate. In this embodiment, the nanotube composition can be used for tracking of imprinted substrates, such as for example, in document security applications. Thus, depositing a SWCNT composition on a substrate, such as a paper document, facilitates visualization/detection of the deposited SWCNT composition via irradiation and detection of a signal, such as an emission from the composition. For example, irradiating the carbon nanotube composition, when the carbon nanotubes are single-walled carbon nanotubes, can be done with a variety of ultra-violet, visible, or near-infrared light sources. Such sources provide the excitation required for fluorescence and can be monochromatic or polychromatic in nature. In an embodiment, the excitation source is a 450 W xenon arc. In other embodiments, the excitation source can be a monochromatic light source in the ultra-violet, visible, or near-infrared such as a solid-state diode laser or some other laser source. In yet another embodiment, a narrow or wideband band light emitting diode with light in the ultra-violet, visible, or near-infrared is used. In an embodiment, detection of MWCNTs and SWCNTs can be done by measuring the electrical conductivity. For example, detection of the emission can be qualitative by using spectral filters and such. Such spectra are typically provided via spectroscopic gratings and NIR detectors. Suitable NIR detectors include detectors based on semiconductors such as InGaAs, silicon, or PbS that may extend to 1.1 μm spectral range or further near-infrared. The ratio of the various emission peaks from different chiralities of SWCNTs may be measured quantitatively.

In an embodiment, the disclosure provides a method for detecting the presence of a single-walled carbon nanotube composition deposited on a substrate from a composition comprising a plurality of the single-walled carbon nanotubes in an aqueous medium, said medium comprising a polyol and a surfactant, wherein the concentration of the nanotubes in the composition is at least 3.6 μg/L and at least 20% of the nanotubes are individually dispersed comprising the steps of: a) obtaining a near infrared spectrum of a sample ink; b) determining if the sample ink has one or more preselected peaks in the near-infrared spectrum; and c) identifying the ink as the single-walled carbon nanotube composition if the sample has one or more preselected peaks in the near-infrared spectrum, wherein the presence of peaks in the near-infrared spectrum indicate the presence of the single-walled carbon nanotube composition. In various embodiments, any suitable reference can be used in place of the sample ink.

For example, the representative characteristic SWCNT emission peaks in the near-infrared include 873 nm, 952 nm, 975 nm, 1023 nm, 1122 nm, 1197 nm, 1250 nm. It is realized by one skilled in the art that these positions of these emission peaks can be slightly shifted in different environment and their relative intensities can be tuned by their relative compositions.

In an embodiment, the presence of the single-walled carbon nanotube composition can be detected after it has been deposited on a substrate. For example, NIR emission spectra of the substrate on which the composition has been deposited can be obtained by standard methods. The spectra can be compared to a reference spectrum for comparison or tracking purposes.

Aspects of the present disclosure facilitate anti-counterfeiting measures whereby compositions of the disclosure can be printed on and/or impregnated into any article at any point of manufacture or distribution of the article. The compositions can accordingly be detected on the article subsequent to its manufacture or distribution to verify a legitimate source of the article via detection of the near infrared signal from the composition, thus authenticating the article. Conversely, for any article which would be expected to have been printed and/or impregnated with a composition of the disclosure, a lack of the near infrared signal from the composition is indicative that the article is inauthentic, such as in the case of a counterfeit article, or an article that has been improperly distributed and/or imported. In embodiments, articles that can be authenticated by detection of the near infrared signal from a composition of the disclosure include but are not necessarily limited to cellulosic articles, such as paper-based products. The paper-based products include but are not necessarily limited to packaging materials, labels, documents and paper currency. In other embodiments, articles that can be authenticated by detecting a composition of the disclosure thereon include but are not necessarily limited to plastic articles. In embodiments, the plastic articles can be any plastic products used in the manufacture of any article, including but not limited to electronic and medical devices and/or plastic parts thereof. In non-limiting embodiments, the plastic articles can include components of pharmaceutical and/or food packaging, such as plastic bottles or other plastic containers. Thus, in various embodiments, applications for the single-walled nanotube composition of the present disclosure can include, for example, authentication of currency, security documents, passports, drivers licenses, identification badges or placards, pharmaceuticals, pharmaceutical packaging, clothing and other consumer goods, books, art, and combinations thereof. The single-walled nanotube composition can be used in quality or process control to identify batches. Additionally, such inks and/or markers could be used in combination with other methods of authentication and identification such as magnetic devices, strips, or labels.

The steps of the methods described in the various embodiments and examples disclosed herein are sufficient to carry out the methods of the present disclosure. Thus, in various embodiments, the methods consists essentially of the combination of the steps of the methods disclosed herein. In various other embodiments, the methods consist of such steps.

In various embodiments, the nanotube composition can be used as a conductive ink, a semiconducting ink, or as a transitive ink depending on the starting SWCNT compositions. These inks may be used in color printing to create functional structures such as circuits and complex patterns with multi-layer information coding for document security applications.

The following examples are presented to illustrate the present disclosure. They are not intended to be limiting in any manner.

EXAMPLE 1

This example discloses a method for dispersing SWCNTs in water at ultra-high concentrations while preserving their unique optical properties. In this example, we used surfactant encapsulation with sodium dodecylbenzene sulfonate (SDBS). By adding sucrose as a co-dispersant to lock the nanotubes in a viscous matrix, SWCNTs can be dispersed to a concentration as high as 3350 mg/L while largely retaining the optical properties characteristic of individually dispersed SWCNTs.

Methods: Solvent Preparation. Sucrose (ACS grade, Mallinkrodt Chemicals) was added to Nanopure™ water (18.2 MΩ) and adjusted to 24.7% w/w using the solution's index of refraction as a reference. SDBS (TCI) was then added at 2% w/v to the solution and dissolved. Control solutions were 2% w/v SDBS in Nanopure water.

Dispersion. Raw HiPco SWCNTs (Unidym Lot #R0513) were added to a stainless steel beaker along with 26 g of solvent (hereafter SWCNT solutions containing SDBS-sucrose are referred to as SWCNTs/SDBS-sucrose samples). Samples without sucrose were used as controls. The SWCNT materials are received as a slurry in ethanol containing 12.3 wt % solid material with approximately 35 wt % metal catalyst/ash impurities. The nanotube mass was adjusted to account for only the solid material and reported as initial nanotube load. The beaker was cooled in a custom refrigerated jacket to 7° C. and subsequently sonicated with a probe tip sonicator (Mysonix 4000: 12.7 mm diameter tip) immersed in the sample. Two stages of sonication were used: 3% amplitude for 30 min followed by 25% amplitude for 1 hr. This first, low-power stage of sonication can replace the traditional high-shear mixing used. A pulsed energy profile (10 s pulses with 2 s dead time) was incorporated for both stages to avoid heating. After sonication, the dispersions were centrifuged at 122 kg for 4 hrs (Beckman Coulter Optima LE-80k) to remove bundled nanotubes and metal particle impurities. The centrifuged tube was separated into 2 fractions: Fraction 1 (top 2 mL) and Fraction 2 (middle 12 mL). Fraction 2 was used for the primary analysis.

Characterization. Solutions were characterized for individual dispersion and concentration using optical absorption, photoluminescence, and Raman spectroscopies. UV-Vis-NIR spectra were collected in the range of 350-1400 nm using a Perkin Elmer Lambda 1050 equipped with a InGaAs detector. All spectra were normalized by diluting with the respective solvent to an absorbance of 0.592 at 500 nm, so that each solution's concentration was in the linear absorption range.

Fluorescence excitation-emission maps were recorded with a Horiba Jobin Yvon NanoLog fluorescence spectrometer using a liquid-$N_2$ cooled InGaAs array detector. Samples were excited in the range of 350-800 nm using a 450 W xenon arc discharge lamp while collecting emission spectra in the range of 800-1500 nm.

Raman spectra were collected with a Horiba Yvon LabRam ARAMIS Raman microscope. The excitation source was a He—Ne (632.8 nm) laser. The samples were drop cast onto a microscope slide and the solvent was allowed to evaporate. Optical images and the corresponding Raman scattering spectra was collected for multiple areas on each sample and compared. Additionally, Raman mapping using the G peak was performed on ink-jet printed samples.

Gravimetric Analysis. The high-concentration solutions were subjected to gravimetric analysis. A fraction of the centrifuged solution was coagulated by addition of ethanol and subsequently filtered with a 1.2 μm pore membrane filter (Millipore Isopore RTTP). The collected solid was washed with a 50/50 mixture of Nanopure water/ethanol and then bath sonicated to re-disperse the cake. This process was repeated 4 times, after which the solid was dispersed in 100% ethanol, filtered (Millipore Fluoropore FGLP 0.2 μm), washed and then dispersed with a minimal volume of dichloromethane. The solvent was evaporated and the remaining solid was dried overnight in a vacuum oven. The mass of this dry material was recorded and the nanotube purity was determined by thermogravimetric analysis using a TA Instruments Q500 Thermogravimetric Analyzer. Samples were heated from 35° C. to 700° C. at 10° C./min in an inert argon atmosphere.

Nanotube Ink. The highest concentration SWCNT/SDBS-sucrose solution (3350 mg/L) was used as an ink to write on various substrates. A technical pen (Kohinoor Rapidograph 300 μm) was used as the writing instrument to give a well-defined line width. This style of pen was chosen due to its removable ink-tank and a pen head that can be disassembled for easy cleaning of all internal components. The aqueous nanotube solution was loaded into the pen after centrifugation as prepared. Writing was performed on substrates including general-purpose laser printing paper (Boise X-9), note cards (Oxford White), Post-It® Notes (3M), adhesive labels (Avery 8160), glass microscope slides (Sailing Boat #7101), and silicon wafers. Control prints were made on the same substrate materials using the SWCNT/SDBS control sample.

Inkjet Printing. A consumer-grade Canon PIXMA MG6120 multifunction printer was used to inkjet-print the nanotube solutions on various paper substrates including Kodak photo paper (Matte), general purpose printing paper (Boise X9), note cards (Oxford White) and Southworth 100% cotton premium resume paper (32 lb Ivory). The original, water-soluble PIXMA ink was flushed from the cartridge with 4 L of Nanopure water followed by 50 mL of isopropyl alcohol. Drying in a vacuum chamber removed traces of the alcohol. Both SWCNT/SDBS-sucrose solutions and the control were used unaltered by loading into individual ink cartridges. Purging removed traces of prior samples from the system.

SWCNT/SDBS-sucrose solutions with nanotube concentrations ranging from 0 mg/L to 800 mg/L were used as ink for inkjet printing. Two test patterns were then printed on paper substrates. The first test pattern (FIG. 16) consisted of text and logos of decreasing size to evaluate how the nanotube ink printed in the inkjet system. The second, a geometric pattern, (FIG. 17) was used to evaluate contrast ratio and fluorescence.

Sucrose Removal. Highly concentrated SWCNT/SDBS-sucrose solutions (~2 g/L) were coated on a polyethylene teraphthalate-cyclohexane dimethanol copolymer (PETG) with a thickness of 50 μm using a modified Mayer Rod coating technique. After drying in an oven at 75° C. for 90 sec, fluorescence of the nanotube film was measured to evaluate whether the film contained individually dispersed nanotubes. The film was then washed with 100% ethanol followed by a gradient of ethanol and water ending with a 1/1 ethanol-water mixture.

Results: High-pressure-carbon-monoxide-synthesized (HiPco) SWCNTs were dispersed in a solution containing 2% SDBS and 24.7% sucrose by ultrasonic processing followed by ultracentrifugation. These solutions were analyzed for retention of optical properties (% individually dispersed) and dispersion yield (the ratio of the post-processed, individually dispersed concentration to the pre-processed concentration) using absorption and fluorescence spectroscopies.

Figure 1:
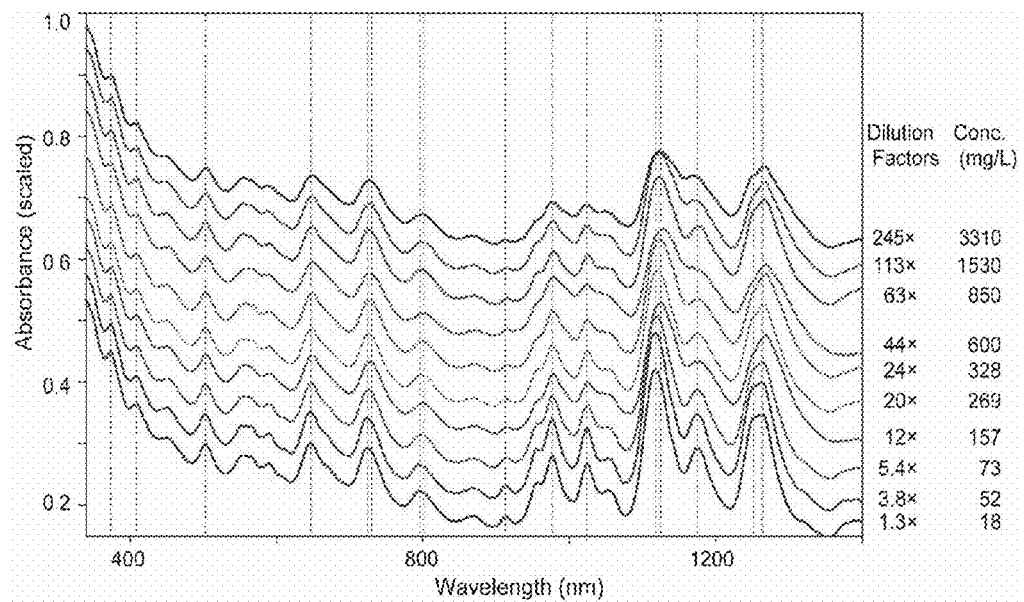
FIG. 1 shows a representative visible-NIR absorption spectra of SWCNTs individually dispersed in sodium dodecylbenzene sulfonate (SDBS)-sucrose solutions. Solutions were diluted to 0.5× the control concentration for comparison (spectra are offset for clarity). Sharp optical features in the visible and NIR regions indicate that SWCNTs are individually dispersed in each solution, even at high concentrations. Vertical dashed lines in FIG. 1 are guides to the eye for comparing peak position and asymmetry (see FIG. 8).

To confirm the presence of individually dispersed nanotubes, we used comparative spectroscopic studies of the SWCNT/SDBS-sucrose dispersions against a low-concentration SWCNT/SDBS control that was prepared using the conventional method. A series of the SWCNT/SDBS-sucrose samples with increasing nanotube concentrations was prepared. The samples were then diluted with SDBS-sucrose solutions to an optical density of 0.5× that of the SWCNT/SDBS control. This dilution was necessary for linear absorption and photoluminescence studies. As the undiluted nanotube concentration was increased by over two orders of magnitude, from 19 mg/L to 3350 mg/L, the diluted samples continued to show the sharp optical absorption peaks in the visible ($E_{22}$ transitions) and the NIR ($E_{11}$ transitions) that are characteristic of individually dispersed SWCNTs (FIGS. 1 and 9). However, these features diminish in intensity and are spectrally broadened at the highest concentrations, indicating the need to monitor for the presence and quantity of nanotube bundles.

Figure 2:
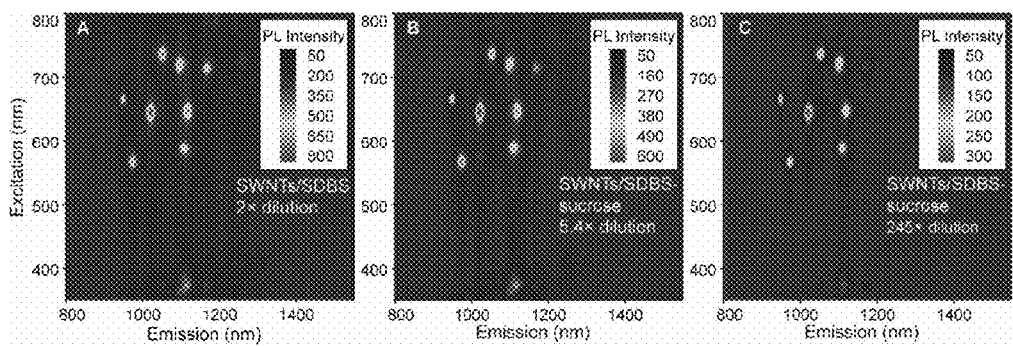
FIG. 2 shows a representative fluorescence excitation-emission maps of SWCNTs in aqueous solutions containing (A) SDBS and (B, C) SDBS and sucrose, normalized to have the same concentration by diluting (A) 2×, (B) 5.4× and (C) 245× relative to their final concentration. Even at the high concentrations, SWCNT/SDBS-sucrose samples show fluorescence that is characteristic of individually dispersed SWCNTs. PL indicates photoluminescence.

Fluorescence spectroscopy is highly sensitive to the electronic state of nanotubes and so can give direct insight into their aggregation, or dispersion state. Emission intensity decreases and peaks broaden with increasing SWCNT bundling. For the SWCNT/SDBS-sucrose samples, excitation-emission maps show consistent peak positions and similar peak shapes for both the diluted SWCNT/SDBS-sucrose dispersions and the control sample (FIG. 2). At the highest concentration (245× dilution), the fluorescence intensity drops to about 35% of that of the control, indicating the presence of at least this percentage of individual nanotubes. To corroborate this high degree of dispersion, the number of individual nanotubes remaining in solution at these high concentrations was estimated by diluting individually dispersed nanotube solutions with bundled solutions. Comparison of the absorption spectra of these mixed solutions (FIG. 10) with those in FIG. 1 indicates that the highly concentrated SWCNT/SDBS-sucrose solutions contain at least 25% individual nanotubes by mass, supporting the estimates from our fluorescence data.

Figure 3:
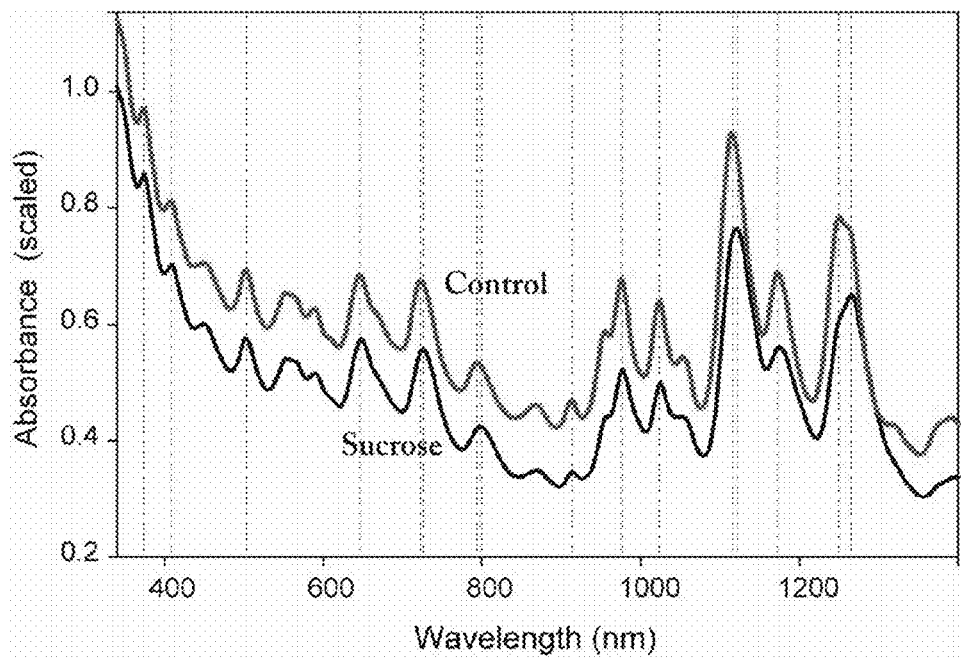
FIG. 3 shows a representative comparison of the visible-NIR absorption spectra of the SWCNT/SDBS-sucrose sample and the control normalized to the same concentration. The absence of blue-shifting in the peaks in the SWCNT/SDBS-sucrose sample is evidence that sucrose is a co-dispersant. The similarities in intensity and peak width show that the sucrose sample is dispersed to a similar degree as the control sample. The spectra are offset for clarity.

To understand the mechanism for the increase in nanotube concentration when sucrose is added during processing, the interaction of sucrose with nanotubes was considered. Previous research has demonstrated the ability of glucose and glycerol to increase the aqueous solubility of DNA and lecithin, respectively, by modifying the hydration layer of the solvent surrounding the solute. However, in the absence of SDBS, sucrose fails to disperse nanotubes in water. When only sucrose is used, the solution is clear after sonication and solid chunks of undispersed nanotube material remain at the bottom of the beaker (FIG. 11). Spectroscopic evidence also suggests that sucrose is unable to interact with nanotubes to an extent great enough for dispersion. In the SDBS-encapsulated control, both the dielectric screening by the SDBS and the π-π interactions between SWCNTs and SDBS decrease the exciton energy gap. Thus, the nanotube absorption and fluorescence peak positions are sensitive to changes in the interactions with surrounding molecules. Sucrose does not contain π-bonds, and so cannot have π-π interactions with carbon nanotubes. Comparison of the absorption spectra of the SWCNT/SDBS control with a SWCNT/SDBS-sucrose sample shows an absence of peak shifts, verifying that sucrose is unable to replace the encapsulating SDBS molecules (FIG. 3). Slight differences in the peak structures can be seen, but these differences can be attributed to statistical variances in the distribution of nanotube chiralities for each sample preparation (FIG. 8). Excitation-emission maps of the samples do not show peak shifts upon the addition of sucrose (FIG. 2). Due to the absence of blue shifts in the spectra when sucrose is present, we can conclude that sucrose does not displace SDBS from the nanotube surface. These observations indicate that sucrose is a co-dispersant as opposed to a co-surfactant.

To provide further insight into the role of sucrose as the co-dispersant, we have tested other potential non-surfactant co-dispersants, including trehalose and glycerol. These species were chosen to mimic the viscosity (glycerol) and molar concentration (trehalose) of the sucrose solution. Our experiments revealed that these substances disperse nanotubes to a similarly high concentration as sucrose. While trehalose is a disaccharide with a size and structure that is similar to that of sucrose, glycerol is a much smaller molecule (FIG. 12). These experiments provide insight into the role of viscosity enhancers in stabilizing nanotubes during ultrasonic processing for efficient surfactant encapsulation.

Figure 4:
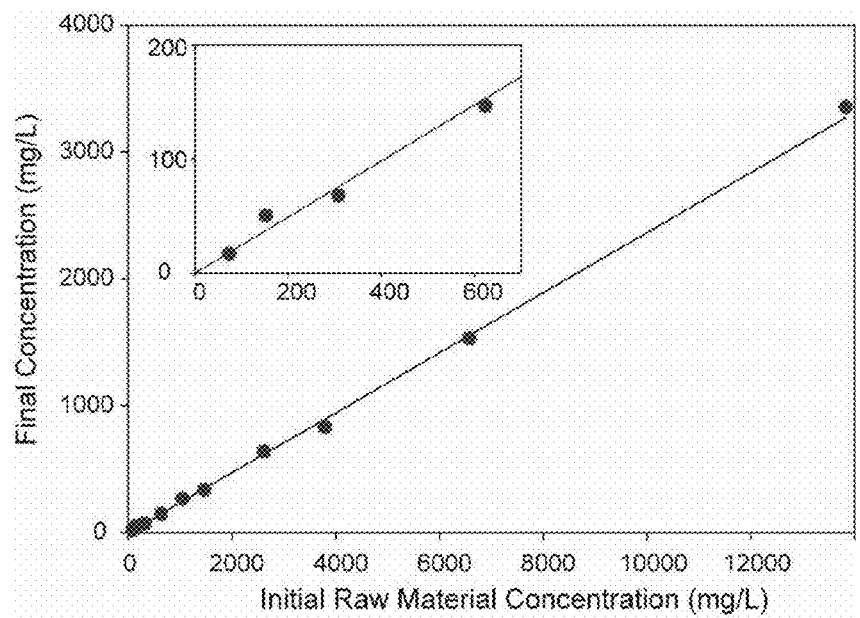
FIG. 4 shows the yield of individually dispersed SWCNTs in an SDBS-sucrose solution as a function of initial nanotube load. The high yield (24%) persists linearly over a range of more than three orders of magnitude in concentration, allowing individually dispersed SWCNT solutions to be prepared in the g/L range by increasing the initial nanotube load. The inset expands on the lower concentration region to show detail.
Figure 5:
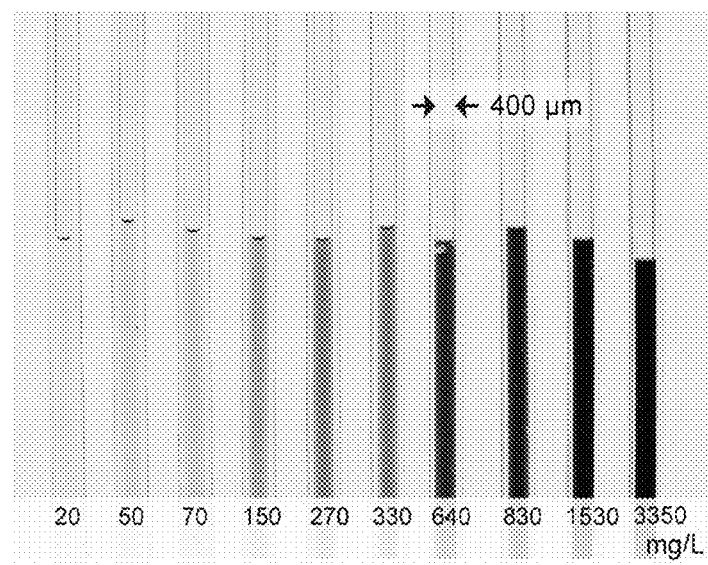
FIG. 5 shows representative capillary tubes containing different concentrations of SWCNTs in an aqueous solvent with both SDBS and sucrose. The samples with the two highest concentrations are visually indistinguishable from one another due to their high absorbances.

The introduction of sucrose with SDBS significantly increases this dispersion yield. We found that sucrose increases the yield to 24%, which is more than a factor of 6 higher than a previous report that used a technique similar as what was used to prepare our control. Our yield remained constant even when the initial nanotube load reached a concentration of 13,800 mg/L (FIG. 4), after which point it became difficult to mix the large amount of nanotubes with the small volume of solvent. This constant yield allows solutions of individually dispersed SWCNTs in the g/L range to be prepared simply by increasing the initial amount of raw material. The highest nanotube concentration achieved has an optical density 124 times higher than those prepared following a conventional method. FIG. 5 shows a photograph of the solutions sealed in capillary tubes with a 400 μm inner diameter. Even with this small optical path length, the most concentrated solutions (1530 and 3350 mg/L) are indistinguishable from one another due to their high optical densities.

Nanotube concentration is typically estimated based on optical absorbance, which is influenced substantially by both composition and aggregation state. The ultrahigh concentrations of our nanotube dispersions enabled us instead to use gravimetric calibration to determine the nanotube concentration. The SWCNT/SDBS-sucrose solutions with the highest concentrations were coagulated and filtered to remove the surfactant and sucrose. The collected pure nanotubes were then weighed to determine both the yield and the final mass concentration after processing. The highest concentration of dispersed SWCNTs achieved was 3350 mg/L.

Due to the high retention of the electronic and optical properties of nanotubes, aqueous solutions of individually dispersed SWCNTs may have broad implications as inks in applications such as document security, anti-counterfeiting measures, and nanotube electronics. We tested the viability of our solutions as SWCNT-based inks for printing on paper and polymer substrates. The 3350 mg/L concentration SWCNT/SDBS-sucrose solution was used in a technical pen to draw lines with widths of 300 μm as defined by the pen on a variety of substrates. The SWCNT/SDBS-sucrose samples had a similar viscosity to the technical pen ink and could be used in the pen unaltered. The high optical density of the nanotube ink gave a large enough contrast ratio on the silicon and paper products that the drawn lines could be seen readily (FIG. 13).

Another advantage of nanotube inks is their compatibility with bottom-up processing using techniques such as inkjet printing. Previous aqueous dispersions of polymer wrapped or functionalized nanotubes have been inkjet-printable but lacked the optical properties of pristine nanotubes due to bundling or sidewall covalent modifications. Nanotubes suspended in organic solvents can also be printed using specialized inkjet systems. However, these solvents are incompatible with the plastic components used in typical consumer-grade inkjet printers. To our knowledge, there have been no reports of inkjet printing patterns of fluorescent nanotube inks with any solvent.

Figure 6:
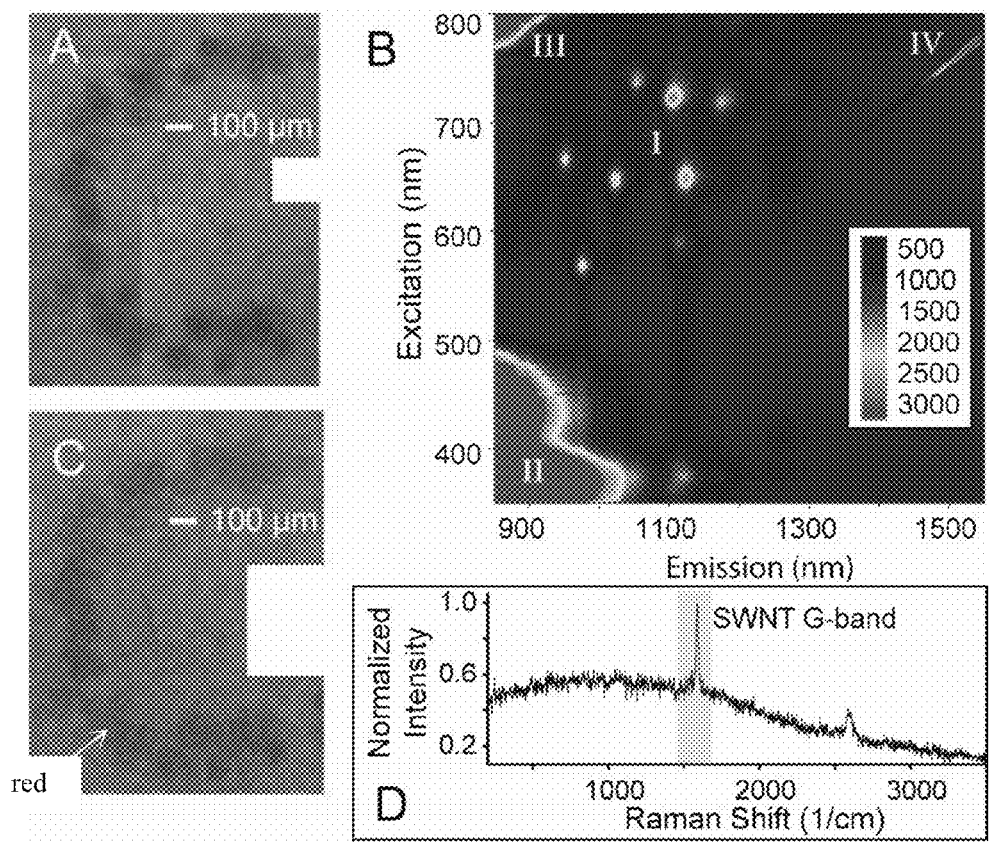
FIG. 6 shows representative inkjet-printed fluorescent features on paper. (A) Composite optical micrograph of the character 'C'. (B) Excitation-emission fluorescence map of a bulk area of the inkjet-printed sample showing the characteristic nanotube fluorescence. The SWCNT fluorescence is in a spectral region (I) that is unimpeded by the substrate fluorescence (II), source reflection (III) and second harmonic reflection (IV). (C) Raman map of the ink-jet printed SWCNT features overlaid on image (A) using the SWCNT G-band shown in (D).

Solutions containing concentrations of nanotubes from 0 mg/L to 800 mg/L were used directly as inks in a consumer-grade inkjet printer (Canon PIXMA MG6120). At nanotube concentrations above 800 mg/L, the viscosity of the solution is too high to allow for consistent, uninterrupted printing in this style of inkjet printer. The character formation from the inkjet drops is consistent across the stock ink, the SWCNT/SDBS-sucrose ink and the SWCNT/SDBS ink (FIG. 14). However, the contrast ratio (blackness) of the SWCNT/SDBS-sucrose ink is much higher than that of the SWCNT/SDBS control. Placement of the SWCNTs can be verified with Raman mapping of the printed characters using the G-band of the SWCNTs (FIG. 6C). Only the SWCNT/SDBS-sucrose sample showed intense nanotube spectral features with fluorescence spectroscopy of the bulk printed area (FIG. 6B). At lower excitation/emission wavelengths broadband fluorescence from the paper substrate saturates the fluorescence map. However, the characteristic NIR fluorescence peaks for the dominant SWCNT species are clearly distinguishable in the unobstructed region of the map. This offset in nanotube fluorescence places the signal in a region unhampered by background and environmental signals, making nanotube ink ideal for applications such as document security.

Figure 7:
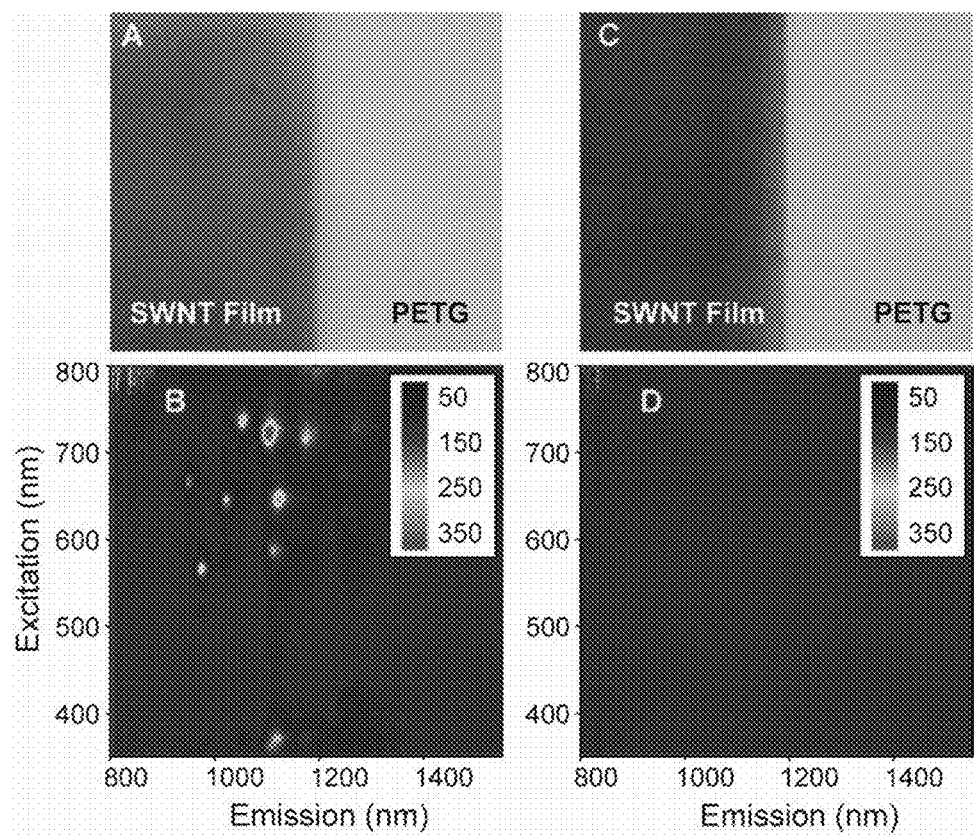
FIG. 7 shows a representative carbon nanotube film produced with a modified Mayer Rod coating technique. (A)

Our sucrose-based nanotube inks can also be used for making thin films. It has been shown that high-concentration solutions of SWCNTs prepared by sonication in SDBS/polyvinylpyrrolidone without centrifugation can form thin films when coated on oxidized silicon surfaces. However, these films crack and become inhomogeneous during solvent evaporation leaving nanotubes suspended across the fissures. Consistent with the literature result, with our control sample the nanotubes tended to coagulate into bundles when the solution was drop-cast and dried on a glass substrate (FIG. 15). When typical nanotube solutions are dried, the high surface tension caused by capillary forces as the solvent front retracts typically leads to nanotube bundling that suppresses the characteristic optical properties of nanotubes, and especially the NIR fluorescence. However, sucrose allows the nanotubes to remain individually dispersed upon drying, even at high concentration. Thus, due to the increased viscosity of the SWCNT/SDBS-sucrose sample, the ink dries into a uniform film (FIG. 15). This feature of the ink not only enables efficient drop casting but also allows for thin films to be created using a modified Mayer Rod coating technique. After casting a thin film using the SWCNT/SDBS-sucrose solution, the sucrose matrix and surfactant can be subsequently removed by washing with ethanol and water. Within the sucrose matrix, the SWCNTs remain individually dispersed even after the thin film dries which is evident by the retention of fluorescent features. When the thin film is washed with ethanol and water the sucrose and surfactant are removed and the nanotubes quickly bundle, which quenches the nanotube fluorescence (FIG. 7).

The addition of viscosity enhancers such as sucrose to aqueous dispersions of SWCNTs with SDBS makes it possible to achieve individually dispersed nanotube concentrations in the g/L range while retaining the nanotube optical properties. Similar effects were observed with other small-molecule viscosity enhancers such as trehalose and glycerol, suggesting the role of solution viscosity in stabilizing aqueous dispersions of carbon nanotubes during processing to provide ultrahigh nanotube concentrations. Due to the retention of optical properties, the nanotube dispersions can be used as fluorescent inks in consumer-grade inkjet printers, technical pens, and other printing techniques such as Mayer Rod coating. The printed structures show strong, well-resolved fluorescence peaks that are characteristic of individually dispersed SWCNTs.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A composition suitable for printing comprising a plurality of carbon nanotubes in an aqueous medium, said medium comprising a polyol and a surfactant, wherein the concentration of the nanotubes in the composition is at least 3.6 μg/L and at least 20% of the nanotubes are individually dispersed.

2. The composition of claim 1, wherein the carbon nanotubes are single-walled carbon nanotubes, multi-walled nanotubes, or a combination thereof.

3. The composition of claim 1, wherein the surfactant is anionic, cationic, nonionic, or a combination thereof.

4. The composition of claim 3, wherein the surfactant is an alkyl sulfonate or alkaryl sulfonate.

5. The composition of claim 1, wherein the polyol is a $C_2$ to $C_{10}$ linear or branched aliphatic polyol, a $C_5$ to $C_{30}$ cyclic or polycyclic aliphatic polyol, or a combination thereof.

6. The composition of claim 5, wherein the polyol is selected from the group consisting of sucrose, trehalose, glycerol, or a combination thereof.

7. The composition of claim 1, wherein the concentration of the polyol in the aqueous medium is 10 to 25% by weight.

8. The composition of claim 1, wherein the concentration of the surfactant in the aqueous medium is 1 to 2% by weight.

9. A substrate having a print on at least a portion thereof, said print made from the composition of claim 1.

10. The substrate of claim 9, wherein the substrate is a coated or uncoated cellulosic material, polymer substrate, glass, metal, silicon, quartz, or a combination thereof.

11. The substrate of claim 10, wherein the cellulosic material is paper.

12. The substrate of claim 10, wherein the polymer substrate is a plastic.

13. A method for detecting the presence of a plurality of single-walled carbon nanotubes deposited on a substrate from a composition comprising a plurality of the single-walled carbon nanotubes in a aqueous medium, said medium comprising a polyol and a surfactant, wherein the concentration of the nanotubes in the composition is at least 3.6 µg/L and at least 20% of the nanotubes are individually dispersed comprising the steps of:
  a) obtaining a near-infrared spectrum of a sample ink;
  b) determining if the sample ink has one or more preselected peaks in the near-infrared spectrum; and
  c) identifying the ink as the single-walled carbon nanotube composition if the sample has one or more preselected peaks in the near-infrared spectrum.

14. The method of claim 13, wherein the carbon nanotube composition is in the form of a film on a substrate.

15. The method of claim 13, wherein the sample ink is present on a cellulosic substrate.

16. The method of claim 15, wherein the cellulosic substrate is paper.

17. The method of claim 13, wherein the sample ink is present on a plastic.

* * * * *